(12) United States Patent
Codony et al.

(10) Patent No.: US 7,410,952 B2
(45) Date of Patent: Aug. 12, 2008

(54) DERIVATIVES OF AZITHROMYCIN

(75) Inventors: Albert Codony, L'Ametlla del Vallès/Barcelona (ES); José Diago, Granollers/Barcelona (ES); Rafael Garcia, Barcelona (ES); Jordi Rifa, Besora/Barcelona (ES)

(73) Assignee: Sandoz AG, Basel (CH)

( * ) Notice: Subject to any disclaimer, the term of this patent is extended or adjusted under 35 U.S.C. 154(b) by 0 days.

(21) Appl. No.: 10/552,318

(22) PCT Filed: Apr. 16, 2004

(86) PCT No.: PCT/EP2004/004053

§ 371 (c)(1), (2), (4) Date: Aug. 7, 2006

(87) PCT Pub. No.: WO2004/092736

PCT Pub. Date: Oct. 28, 2004

(65) Prior Publication Data

US 2007/0043214 A1    Feb. 22, 2007

Related U.S. Application Data

(60) Provisional application No. 60/511,282, filed on Oct. 15, 2003, provisional application No. 60/463,600, filed on Apr. 17, 2003.

(51) Int. Cl.
*A61K 31/70* (2006.01)
*C07H 17/08* (2006.01)

(52) U.S. Cl. .......................... 514/29; 536/7.4

(58) Field of Classification Search ................... 536/7.4
See application file for complete search history.

(56) References Cited

U.S. PATENT DOCUMENTS 3,725,385 A    4/1973    Freiberg
6,764,997 B2 *  7/2004    Tenengauzer et al. ......... 514/29

FOREIGN PATENT DOCUMENTS

WO    WO 00/42055 A    7/2000

OTHER PUBLICATIONS

Hunter, R.P. et al., "Azithromycin metabolite identification in plasma, bile, and tissues of the ball python (*Pythlon regius*)", Journal of Veterinary Pharmacology and Therapeutics, vol. 26(2), pp. 117-121 (2003).
Debremaeker, D. et al., "Analysis of unknown compounds in azithomycin bulk samples with liquid chromatography coupled to ion mass spectrometry", Rapid Communication in Mass Spectrometry, vol. 17(4), pp. 342-350 (2003).
Pharmeuropa, vol. 13, No. 4, pp. 750-754 (2001).

* cited by examiner

*Primary Examiner*—Elli Peselev
(74) *Attorney, Agent, or Firm*—Luedeka, Neely & Graham, P.C.

(57) ABSTRACT

The invention relates to derivatives of azithromycin, processes for the manufacture thereof and pharmaceutical compositions thereof preferably together with azithromycin.

5 Claims, No Drawings

DERIVATIVES OF AZITHROMYCIN

This application is a 371 of International Application No. PCT/EP 2004/004,053 filed Apr. 16, 2004, which claims the benefit of Provisional Application No. 60/463,600 filed Apr. 17, 2003 and Provisional Application No. 60/511,282 filed Oct. 15, 2003, which is incorporated herein by reference.

The present invention relates to new derivatives of azithromycin, a process for preparing these new derivatives and pharmaceutical compositions containing at least one new azithromycin derivative preferably together with azithromycin.

Azithromycin (formula 1) is a well-known antibacterial agent, described e.g. in the Merck Index, 13th edition (2001), page 159 (917).

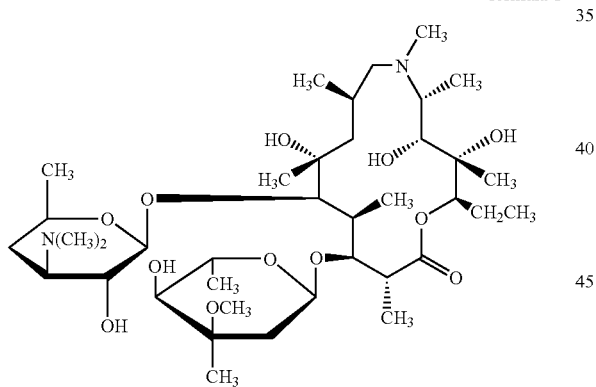

formula 1

The present applicants have found that new derivatives of azithromycin with valuable properties may be obtained by using azithromycin as starting material.

Accordingly, one embodiment of the present invention relates to new azithromycin derivatives selected from the group of 3'-(N,N-didemethyl)-3'-N-formylazithromycin of formula 2,

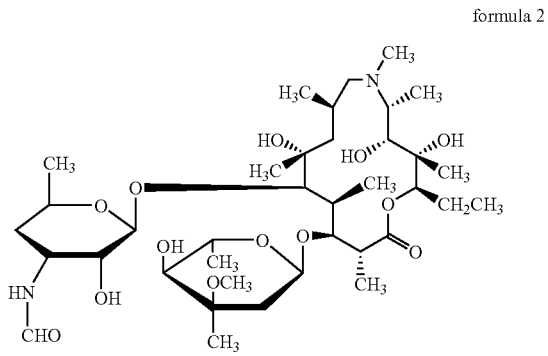

formula 2

3'-N-demethyl-3'-N-formylazithromycin of formula 3,

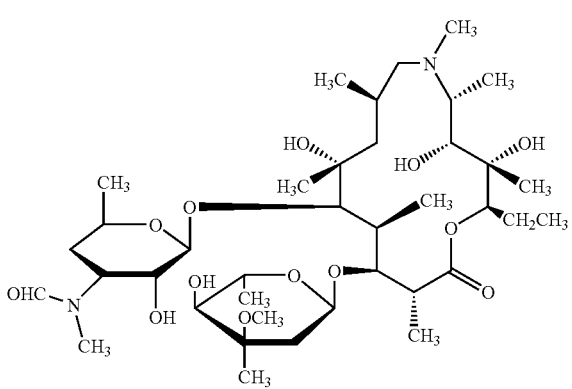

formula 3

3'-ketoazithromycin(3'-de(dimethylamino)-3'-oxoazithromycin) of formula 4,

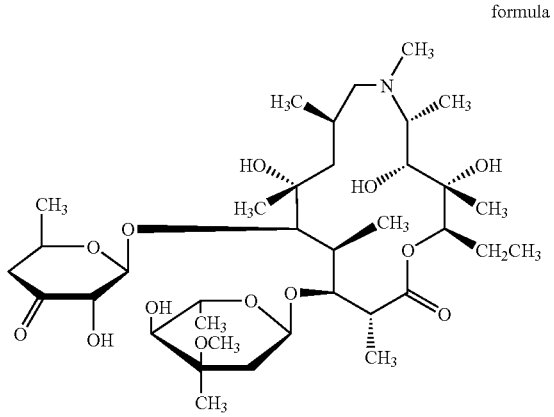

formula 4

3'-aminoazithromycin(3'-(N,N-didemethyl)azithromycin) of formula 6,

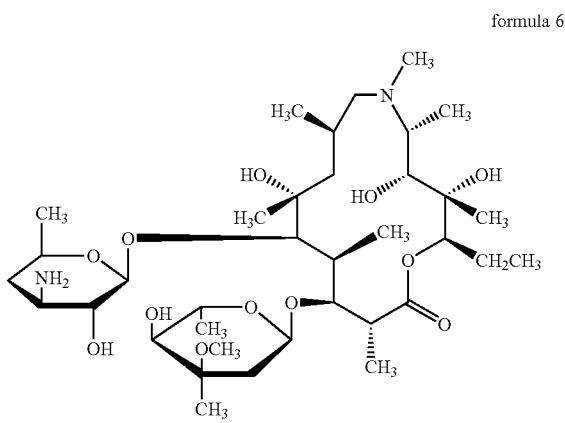

formula 6

3'-de(dimethylamino)-3',4'-didehydroazithromycin of formula 7,

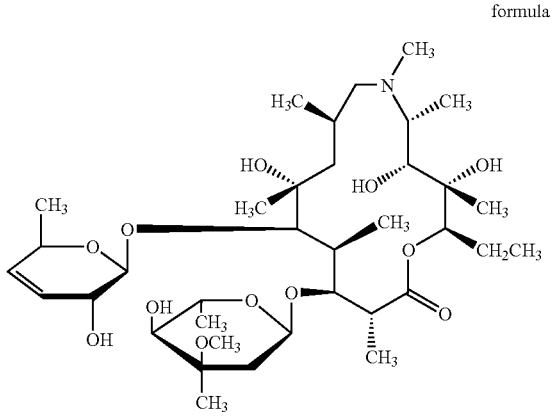

formula 7 and
(3R,6R,8R,9R,10S,11S,12R)-11-[(2,6-dideoxy-3-C-methyl-3-O-methyl-α-L-ribo-hexopyranosyl)oxy]-2-[(1R,2R)-1,2-dihydroxy-1-methylbutyl]-8-hydroxy-3,4,6,8,10,12-hexamethyl-9-[(3,4,6-trideoxy-3-(dimethylamino)-β-D-xylo-hexopyranosyl)oxy]-1-oxa-4-azacyclotridecan-13-one of formula 8

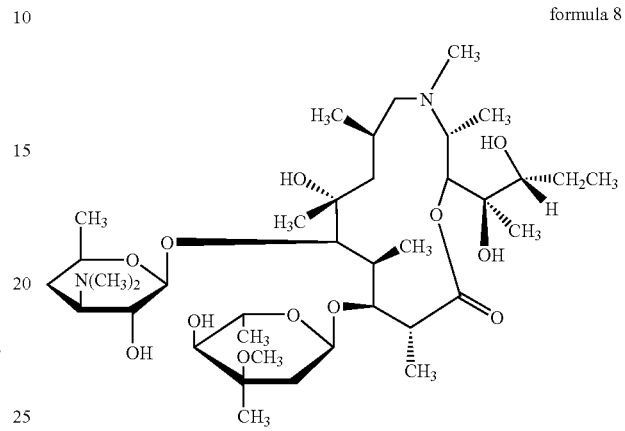

formula 8

The derivatives mentioned above are in form of a base or an acid addition salt, e.g. in the form of a pharmaceutically acceptable salt, e.g. in the form of a hydrochloride, hydrobromide or thiocyanate.

In a further embodiment, the present invention relates to a process for preparing the above mentioned azithromycin derivatives starting from azithromycin.

A suitable starting material includes any azithromycin salt or base in any crystalline, polymorphic or amorphous form, e.g. an azithromycin monohydrate as disclosed e.g. in U.S. Pat. No. 4,517,359, WO 01/00640, WO 02/094843 or WO 02/10181, any azithromycin dihydrate as disclosed e.g. in EP 0298650, WO 01/87912 or WO 02/094843, or any azithromycin clathrate as disclosed e.g. in EP 0984020 or WO 02/085898.

3'-Aminoazithromycin (the compound of formula 6) may be obtained by demethylation of azithromycin with iodine and sodium acetate according to a similar method described for erythromycin in U.S. Pat. No. 3,725,385 resulting in N-demethylazithromycin(3'-N-demethyl-azithromycin). Subsequently N-demethylazithromycin may be oxidized with an oxidant such as iodine and sodium metoxide.

3'-(N,N-didemethyl)-3'-N-formylazithromycin (the compound of formula 2) may be obtained by formylation of 3'-aminoazithromycin (compound of formula 6) using a mixed anhydride technique. Preferably a mixed anhydride obtained by mixing acetic anhydride and formic acid is used. The formylation can be carried out in presence of a base in an aprotic solvent, e.g. in diethyl ether or dichloromethane.

3'-Ketoazithromycin (the compound of formula 4) may be obtained by oxidation of 3'-aminoazithromycin (the compound of formula 6) with an oxidant such as sodium hypochlorite. Optionally, the oxidation may be carried out in the presence of a catalyst, e.g. a metalloporphyrin, e.g. 5,10,15,20-tetraphenyl-21H, 23H-porphine iron (III) chloride.

3'-N-demethyl-3'-N-formylazithromycin (the compound of formula 3) may be obtained by formylation of N-demethylazithromycin using a mixed anhydride technique. Similar conditions to those described for the compound of formula 2 may be employed.

Azithromycin N-oxide of formula 5

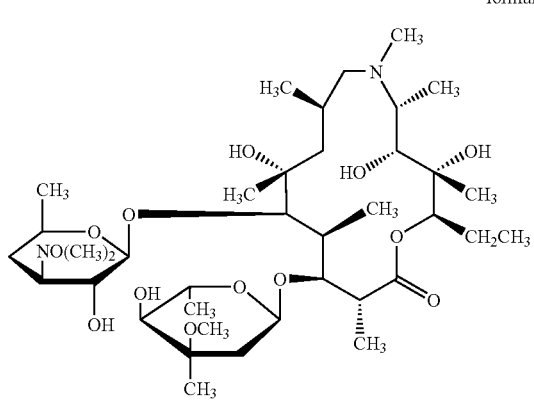

formula 5 may be obtained by oxidation of an azithromycin with an oxidant such as hydrogen peroxide in methanol.

Thermal decomposition of azithromycin N-oxide, optionally performed in a solvent medium such as dimethylformamide, results in 3'-de(dimethylamino)-3',4'-didehydroazithromycin (the compound of formula 7).

The new azalide (3R,6R,8R,9R,10S,11S,12R)-11-[(2,6-dideoxy-3-C-methyl-3-O-methyl-α-L-ribo-hexopyranosyl)oxy]-2-[(1R,2R)-1,2-dihydroxy-1-methylbutyl]-8-hydroxy-3,4,6,8,10,12-hexamethyl-9-[(3,4,6-trideoxy-3-(dimethylamino)-β-D-xylo-hexopyranosyl)oxy]-1-oxa-4-azacyclotridecan-13-one (the compound of formula 8), may be obtained by dissolving azithromycin (the compound of formula 1) in a polar solvent medium e.g. acetonitrile and water, methanol and water or ethanol and water. Alternatively, the new azalide of formula 8 may be obtained by overdrying azithromycin (the compound of formula 1).

Under these conditions azithromycin may be partially transformed into azalide of formula 8 in a percentage of at least 0.1% by weight, especially of at least 0.5% by weight.

Both the azalide of formula 8 and azithromycin (compound of formula 1) may exist as equilibrium of isomers, which are encompassed by the present invention.

Optionally the azalide of formula 8 can be isolated by chromatography, e.g. Silicagel 60, ethyl acetate:hexane:diethylamine 5:5:1 (by volume).

In an alternative aspect of the present invention, the azithromycin derivative of formula 8 may be obtained by methylation of the nitrogen atom in position 4 of the ring structure of an azalide of formula 9

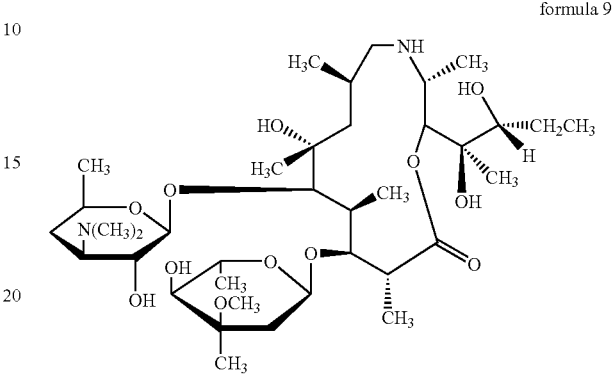

formula 9 using a methylating agent, e.g. methyl iodide, and a base, e.g. potassium carbonate.

This is surprising, because until now the attempts to produce the azalide of formula 8 by methylation have failed, e.g as disclosed in Tetrahedron, Vol 53, No. 50, 16923-16944, 1997, wherein the product finally obtained by an Eschweiler-Clarke methylation was an azalide of formula 10 as seen below:

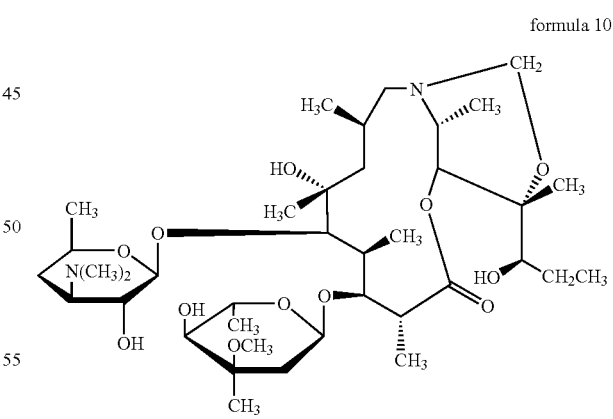

formula 10

The azalide of formula 9 may be obtained by dissolution of an azalide of formula 11 formula 11

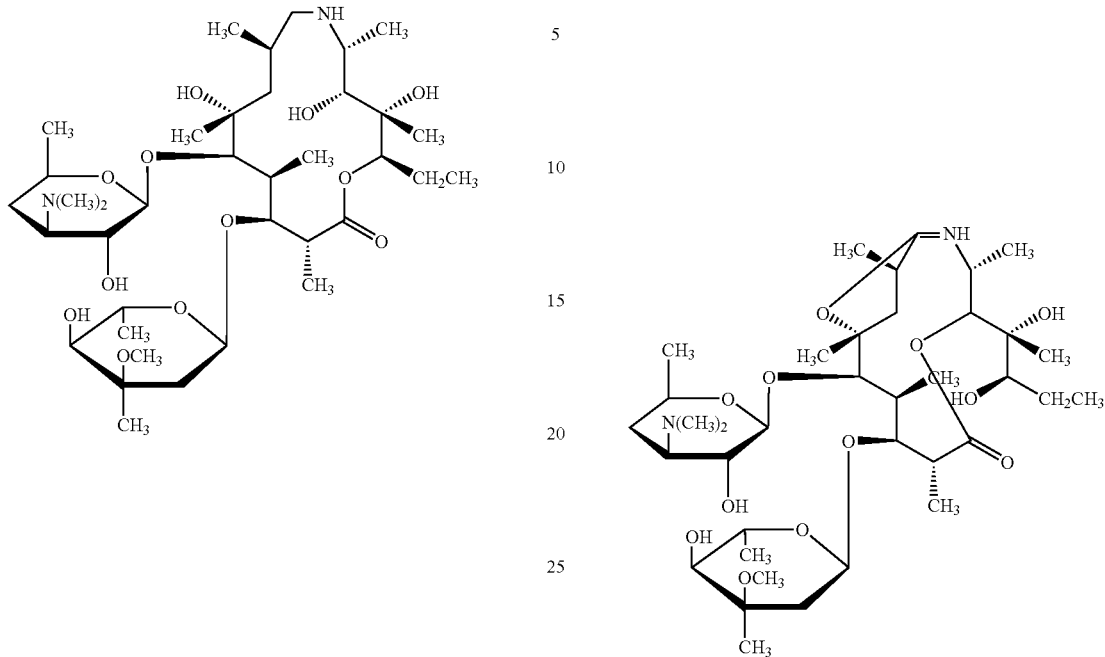

in a polar solvent medium, e.g. acetonitrile and water, 40:60 (by volume).

Another possibility to obtain a compound of formula 9 could be the method described in Tetrahedron, Vol 53, No. 50, 16923-16944, 1997, wherein a compound of the formula

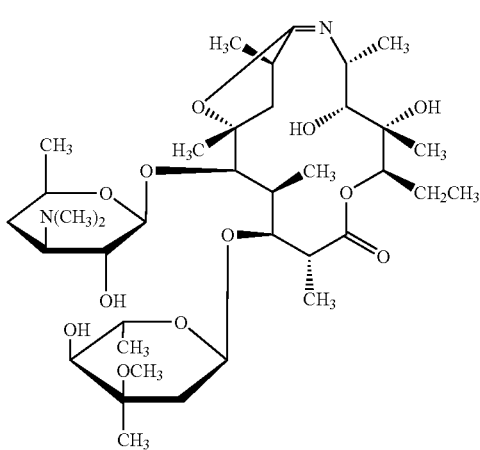

is converted using e.g. lithium hydroxide in ethanol, into a compound of the following formula which may subsequently be reduced to give inter alia a compound of formula 9.

In a further aspect of the present invention, the new azithromycin derivative of formula 8 can be optionally obtained as mixed with azithromycin when the methylation is carried out using a mixture of the azalide of formula 9 and an azalide of formula 11.

In an additional aspect, the present invention relates to pharmaceutical compositions comprising at least one new azithromycin derivative of formula 2, 3, 4, 6, 7 or 8, preferably together with any azithromycin salt or base in any crystalline, polymorphic or amorphous form.

The weight ratio of one or more of the new azithromycin derivative/s to any azithromycin salt or base may vary from 0.1 to 99.

EXAMPLES

All temperatures are given in degree Celsius and are uncorrected.

MS means mass spectrometry

APCI means Atmospheric Pressure Chemical Ionization

HPLC means High Performance Liquid Chromatography

Example 1

Preparation of 3'-N-demethyl-3'-N-formylazithromycin (Compound of Formula 3)

28.6 ml of freshly prepared formic acetic anhydride are added slowly (30 minutes) from a dropping funnel to a stirred suspension of N-demethylazithromycin (18.3 g) and $K_2CO_3$ (10.0 g) in 500 ml of diethyl ether at 0-5° C. The reaction mixture is heated to room temperature in 5 minutes and stirred for 5 additional minutes. 500 ml of water are added and the resulting mixture is shaken. The ethereal layer is discarded and the aqueous layer is extracted with chloroform (3×150 ml). Organic layers are combined, dried over $Na_2SO_4$ and evaporated to dryness to give a white solid. The solid obtained is treated with acetone (100 ml) and heated to reflux. The residue insoluble is filtered off and water (200 ml) is added drop-wise (30 minutes) to the solution at 50° C. The suspension is stirred for 30 minutes at 50° C., allowed to cool to 20° C. and stirred for 30 minutes. The solid precipitated is filtered and re-crystallized twice following the same process to give a solid that suspended in hexane affords 4.5 g of 3'-N-demethyl-N-formylazithromycin.

MS analysis (APCI) of 3'-N-demethyl-N-formylazithromycin ([m+H] at m/z 763) shows losses of cladinose at m/z 605, cladinose and water at m/z 587, cladinose and modified desosamine at m/z 434, and sequential losses of one water (m/z 416) and two molecules of water (m/z 398) from fragment at m/z 434.

Example 2

Preparation of 3'-Aminoazithromycin (Compound of Formula 6)

7.1 g of iodine are added to a solution of 4.0 g of N-demethylazithromycin and 5.1 ml of sodium methoxide (30% in methanol) in methanol (300 ml) cooled to 0-5° C. The solution is kept at 0-5° C. for 90 minutes. The reaction mixture is poured into a solution of sodium thiosulfate pentahydrate (18.83 g) and 25% $NH_3$ (12.0 ml) in 1500 ml of water cooled to 0-5° C. The resulting solution is stirred for 10 minutes and extracted twice with 100 ml of $CHCl_3$. The combined chloroform layers are washed with water (100 ml) containing 5% of concentrated ammonia solution, dried over anhydrous sodium sulphate and evaporated under reduced pressure to give a white foam (3.9 g). This material is dissolved in a mixture of 100 ml of methylene chloride and 125 ml of water. The water layer is extracted with 50 ml of methylene chloride. The combined organic layers are concentrated to dryness to yield a residue which on re-crystallization from methanol affords 1.7 g of 3'-aminoazithromycin.

MS analysis (APCI) of 3'-aminoazithromycin ([m+H] at m/z 721) shows losses of modified desoamine moiety at m/z 592, cladinose at m/z 563, cladinose and water at m/z 545, cladinose and modified desosamine at m/z 434, and sequential losses of one water (m/z 416) and two molecules of water (m/z 398) from fragment at m/z 434.

Example 3

Preparation of 3'-(N,N-didemethyl)-3'-N-formylazithromycin (Compound of Formula 2)

2.0 ml of freshly prepared formic acetic anhydride are added drop-wise (5 minutes) from a dropping funnel to a stirred suspension of 3'-aminoazithromycin (4.0 g) and $K_2CO_3$ (2.2 g) in 111 ml of diethyl ether at 0-5° C. The reaction mixture is allowed to warm to ambient temperature and stirred for 25 minutes. 111 ml of cooled water (0-5° C.) are added (10 min) to the reaction mixture at room temperature. The ethereal layer is discarded and the aqueous layer is extracted with chloroform (3×66 ml). Organic layers are combined and washed with water at pH 6. Water (150 ml) is added to the organic layer and the mixture is adjusted to pH 5 with formic acid. The organic layer is discarded. The water layer is adjusted to pH 8.8 and extracted twice with ethyl acetate (2×150 ml). The combined organic layers are dried over $Na_2SO_4$, filtered and concentrated on a rotatory evaporator to give 1.7 g of a solid. The residue is dissolved in 3 ml of a mixture of hexane:ethyl acetate:diethylamine (10:10:2, by volume) and purified through a silica gel (150.0 g, 230-400 mesh) column (150.0 g, 50×5 cm) eluting with the same mixture of solvents. The fractions containing the title compound are combined and evaporated to dryness to give a slightly yellow foam (1.1 g). The residue is treated with hexane to afford 0.9 g of 3'-(N,N-didemethyl)-3'-N-formylazithromycin.

MS analysis (APCI) of 3'-(N,N-didemethyl)-3'-N-formylazithromycin ([m+H] at m/z 749) shows losses of cladinose at m/z 591, cladinose and water at m/z 573, cladinose and modified desosamine at m/z 434, and sequential losses of one water (m/z 416) and two molecules of water (m/z 398) from fragment at m/z 434

Example 4

Preparation of 3'-Ketoazithromycin (Compound of Formula 4)

A solution of 3'-aminoazithromycin (0.90 g) in dichloromethane is treated with 10 mg of 5,10,15,20-tetraphenyl-21H, 23H-porphine iron (III) chloride, an aqueous 5% solution of NaOCl (3 ml) and pyridine (0.025 ml) and the reaction mixture is stirred at room temperature with repeated periodic charges of NaOCl solution (2.5 ml) until starting material content in reaction mixture is lower than 10%. The organic layer is separated and evaporated to dryness to afford 0.94 g of a deep red crude solid. The crude is chromatographed (300 g silicagel 60, 230-400 mesh, 50×5 cm) using hexane:ethyl acetate:diethylamine (10:10:2, by volume) giving 0.176 g of a brown solid which is dissolved in toluene (25 ml). Toluene solution is washed with water (25 ml) at pH 10.5 and 7. Finally, organic layer is extracted twice with water at pH 6 and 5.5. Organic phase is discarded and aqueous layers at pH 5.5 and 6 are combined, the pH adjusted to 11 and extracted twice with isopropyl acetate (50 ml). The organic layer is separated and evaporated to dryness to give 0.098 g of 3'-ketoazithromycin.

MS analysis (APCI) of 3'-ketoazithromycin ([m+H] at m/z 720) shows losses of cladinose at m/z 562, cladinose and water at m/z 544, cladinose and modified desosamine at m/z 434, and sequential losses of one water (m/z 416) and two molecules of water (m/z 398) from fragment at m/z 434.

Example 5

Preparation of Azithromycin N-oxide (Compound of Formula 5)

250 ml of 30% $H_2O_2$ are added drop-wise (5 minutes) to a solution of azithromycin dihydrate (50.0 g) in methanol (200 ml) at room temperature. The resulting solution is stirred for 2 hours. Chloroform is added (250 ml) and the resulting mixture is shaken. The aqueous layer is back extracted twice with chloroform (125 ml). Organic layers are combined, washed with water (5×500 ml), dried over Na$_2$SO$_4$ and evaporated to dryness. The residue obtained is treated with hexane (800 ml) to afford 35.3 g of crystals of azithromycin N-oxide.

MS analysis (APCI) of azithromycin N-oxide ([m+H] at m/z 765) shows losses of dimethyl-hydroxylamine at m/z 704, cladinose at m/z 607, cladinose and dimethylhydroxylamine at m/z 546, cladinose, dimethylhydroxylamine and modified desosamine at m/z 434, and sequential losses of one water (m/z 416) and two molecules of water (m/z 398) from fragment at m/z 434.

Example 6

Preparation of 3'-de(dimethylamino)-3',4'-didehydroazithromycin (Compound of Formula 7)

A solution of azithromycin N-oxide (33.1 g) in dimethylformamide (500 ml) is heated at 130-140° C. for 2 hours 15 minutes. The solvent is distilled off under reduced pressure, acetonitrile is added to the residue and the suspension is stirred. The solid precipitated is filtered and treated with water at 90° C. and refluxing acetonitrile. The insoluble solid is collected by filtration and dried to give 16.6 g of 3'-de(dimethylamino)-3',4'-didehydroazithromycin.

MS analysis (APCI) of 3'-de(dimethylamino)-3',4'-didehydroazithromycin ([m+H] at m/z 704) shows losses of cladinose at m/z 546, cladinose and water at m/z 528, cladinose and modified desosamine at m/z 434, and loss of one water molecule (m/z 416) from fragment at m/z 434.

Example 7

Preparation of (3R,6R,8R,9R,10S,11S,12R)-11-[(2,6-dideoxy-3-C-methyl-3-O-methyl-α-L-ribo-hexopyranosyl)oxy]-2-[(1R,2R)-1,2-dihydroxy-1-methylbutyl]-8-hydroxy-3,4,6,8,10,12-hexamethyl-9-[(3,4,6-trideoxy-3-(dimethylamino)-β-D-xylo-hexopyranosyl)oxy]-1-oxa-4-azacyclotridecan-13-one (Compound of Formula 8)

49.10 mg of azithromycin (compound of formula 1) as dihydrate are dissolved in 25 ml of a mixture of ethanol and water (40:60, by volume). HPLC analysis of the obtained solution after 24 hours gives a content of the azalide of formula 8 of 1.2% by weight.

MS analysis (APCI) of azalide of formula 8 ([M+H] at m/z 749) shows the sequential losses of 158 and 157 to form two abundant ions at 591 and 434, respectively. The products ions are generated by the subsequent losses of cladinose and desosamine. A similar fragmentation pattern is observed for azithromycin.

Example 8

Preparation of (3R,6R,8R,9R,10S,11S,12R)-11-[(2,6-dideoxy-3-C-methyl-3-O-methyl-α-L-ribo-hexopyranosyl)oxy]-2-[(1R,2R)-1,2-dihydroxy-1-methylbutyl]-8-hydroxy-3,4,6,8,10,12-hexamethyl-9-[(3,4,6-trideoxy-3-(dimethylamino)-β-D-xylo-hexopyranosyl)oxy]-1-oxa-4-azacyclotridecan-13-one (Compound of Formula 8)

15.0 g of azithromycin (compound of formula 1) are dried under vacuum for 6 hours at 70° C. in order to anhydrify the product. After anhydrification the product is heated at 80° C. in contact with air. This process is repeated several times. After several cycles a mixture of the azalide of formula 8 and azithromycin are obtained.

The content of azalide 8 in the mixture is higher than 3% by weight.

MS analysis (APCI) of azalide of formula 8 ([M+H] at m/z 749) shows the sequential losses of 158 and 157 to form two abundant ions at 591 and 434, respectively. The products ions are generated by the subsequent losses of cladinose and desosamine. A similar fragmentation pattern is observed for azithromycin.

The invention claimed is:

1. A derivative of azithromycin as base or in the form of an acid addition salt which is 3'-(N,N-didemethyl)-3'-N-formylazithromycin of formula 2.

2. A pharmaceutical composition comprising the derivative of azithromycin according to claim 1.

3. A pharmaceutical composition according to claim 1 comprising a mixture of i) the derivative of azithromycin according to claim 1, and ii) any azithromycin base or salt in any crystalline, polymorphic or amorphous form, wherein the weight ratio of the at least one derivative described in i) and azithromycin as described in ii) is between 0.1 and 99.

4. A process for preparing 3'-(N,N-didemethyl)-3'-N-formylazithromycin of formula 2 comprising formylation of 3'-aminoazithromycin of formula 6.

5. A process according to claim 4 wherein the formylation of 3'-aminoazithromycin is carried out by using formic acetic anhydride.

\* \* \* \* \*